US009511154B2

(12) United States Patent
Aime et al.

(10) Patent No.: US 9,511,154 B2
(45) Date of Patent: *Dec. 6, 2016

(54) PROCESS FOR THE PREPARATION OF HYPERPOLARIZED DERIVATIVES FOR USE IN MRI ANALYSIS

(71) Applicant: BRACCO IMAGING S.P.A., Milan (IT)

(72) Inventors: Silvio Aime, Carignano (IT); Sonia Colombo Serra, Vigliano Biellese (IT); Giovanni Battista Giovenzana, Novara (IT); Pernille Rose Jensen, Copenhagen (DK); Magnus Karlsson, Malmo (SE); Mathilde H. Lerche, Frederiksberg C (DK); Fabio Tedoldi, Marzano (IT)

(73) Assignee: BRACCO IMAGING S.P.A., Milan (IT)

( * ) Notice: Subject to any disclaimer, the term of this patent is extended or adjusted under 35 U.S.C. 154(b) by 369 days.

This patent is subject to a terminal disclaimer.

(21) Appl. No.: 14/350,478

(22) PCT Filed: Oct. 11, 2012

(86) PCT No.: PCT/EP2012/070187
§ 371 (c)(1),
(2) Date: Apr. 8, 2014

(87) PCT Pub. No.: WO2013/053839
PCT Pub. Date: Apr. 18, 2013

(65) Prior Publication Data
US 2014/0257085 A1 Sep. 11, 2014

(30) Foreign Application Priority Data
Oct. 12, 2011 (EP) .................... 11184825

(51) Int. Cl.
A61K 49/10 (2006.01)
G01R 33/56 (2006.01)

(52) U.S. Cl.
CPC ........... A61K 49/10 (2013.01); G01R 33/5601 (2013.01)

(58) Field of Classification Search
None
See application file for complete search history.

(56) References Cited

U.S. PATENT DOCUMENTS

| 6,466,814 | B1 | 10/2002 | Ardenkjaer-Larsen et al. | |
|---|---|---|---|---|
| 2002/0004072 | A1 | 1/2002 | Thomas | |
| 2008/0095713 | A1 | 4/2008 | Thaning | |
| 2008/0287774 | A1 | 11/2008 | Katz-Brull | |
| 2008/0292551 | A1* | 11/2008 | Thaning | A61K 49/10 424/1.81 |
| 2009/0148432 | A1 | 6/2009 | Higuchi | |
| 2010/0190967 | A1 | 7/2010 | Gloegaard et al. | |
| 2013/0096420 | A1* | 4/2013 | Aime | A61K 49/10 600/420 |

FOREIGN PATENT DOCUMENTS

| EP | 1544634 A1 | 6/2005 |
|---|---|---|
| JP | 2009527768 | 7/2009 |
| WO | 88-10419 A1 | 12/1988 |
| WO | 90-00904 A1 | 2/1990 |
| WO | 91-12024 A1 | 8/1991 |
| WO | 93-02711 A1 | 2/1993 |
| WO | 96-39367 A1 | 12/1996 |
| WO | 98-58272 A1 | 12/1998 |
| WO | 9924080 A1 | 5/1999 |
| WO | 99-35508 A1 | 7/1999 |
| WO | 01-96895 A1 | 12/2001 |
| WO | 0237132 | 5/2002 |
| WO | 2007044867 A2 | 4/2007 |
| WO | 2007-064226 A2 | 6/2007 |
| WO | 2007136439 A2 | 11/2007 |
| WO | 2010037771 A1 | 4/2010 |
| WO | 2011-124672 A1 | 10/2011 |

OTHER PUBLICATIONS

PCT International Preliminary Report on Patentability for PCT/EP2012/070187, mail date Apr. 15, 2014.
PCT international Search Report for PCT/EP2012/070187, mail date Dec. 4, 2012.
PCT Written Opinion for PCT/EP2012/070187, mail date Dec. 4, 2012.
Gallagher, Ferdia A. et al., "Production of hyperpolarized [1,4-13C2]malate from [1,4-13C2]furmarate is a marker of cell necrosis and treatment response in tumors", Proceedings of the National Academy of Sciences, Jan. 1, 2009, XP055045201, ISSN: 0027-8424, DOI: 10.1073/pnas.0911447106, pp. 19801-19806.
Gallagher, Ferdia A. et al., "Detection of tumor glutamate metabolism in vivo using 13C magnetic resonance spectroscopy and hypepolarized [1-13C]glutamate", Magnetic Resonance in Medicine, vol. 66, No. 1, Feb. 17, 2011, pp. 18-23, XP055045198, ISSN: 0740-3194, DOI: 10.1002/mrm.22851.
Viale, Alessandra et al., "Current concepts on hyperpolarized molecules in MRI", Current Opinion in Chemical Biology, Current Biology Ltd., London, GB, vol. 14, No. 1, Feb. 1, 2010, pp. 90-96, XP026895607, ISSN: 1367-5931, DOI: 10.1016/J.CBPA.2009.10.021.
Wilson, David M. et al., "Generation of hyperpolarized sustrates by secondary labeling with [1,1-C-13] acetic anhydride", Proceedings of Teh National Academy of Sciencies of USA, National Academy of Science, Washington, DC; US, vol. 106, No. 14, Apr. 7, 2009, pp. 5503-5507, XP002641409, ISSN: 0027-8424, DOI: 10.1073/PNAS.08109106.

(Continued)

Primary Examiner — Michael G Hartley
Assistant Examiner — Jennifer Lamberski
(74) Attorney, Agent, or Firm — Vivicar Law, PLLC

(57) ABSTRACT

The present invention relates to a process for the preparation of aqueous solutions of hyperpolarized carboxylic organic acids ready for use in in-vivo MR diagnostic imaging, and the use of the corresponding anhydrides or esters as glass-forming agents.

10 Claims, 3 Drawing Sheets

(56) References Cited

OTHER PUBLICATIONS

Aime, Silvio et al., "Synthesis and NMRD Studies of Gd3+ Complexes of Macrocyclic Polyamino Polycarboxylic Ligands Bearing beta-Benzyloxy-alpha-propionic Residues", Inorganic Chemistry, American Chemical Society, Easton, US, vol. 31, No. 6, Mar. 18, 1992, pp. 1100-1103, XP002120082, ISSN: 0020-1669, DOI: 10.1021/IC00032A035.
Application, National Phase of PCT/EP2012/074292 WO2013/083535A1), U.S. Appl. No. 14/362,447, filed Jun. 3, 2014, with Preliminary Amendment, filed Jun. 4, 2014.
European Search Report for European application No. EP11184825.5, mail date Feb. 10, 2012.
European Search Report for European application No. EP11191872.8, mail date Apr. 12, 2012.
Hovland, Ragnar et al., "Preparation and In Vitro Evaluation of Godota-(BOM)4; A Novel Angiographic MRI Contrast Agent", Org. Biomol Chem., vol. 1, Apr. 10, 2003, pp. 1707-1710, XP002672385.
PCT International Search Report for PCT/EP2012/074292, mail date Jan. 30, 2013.
PCT Written Opinion for PCT/EP2012/074292, mail date Jan. 30, 2013.
PCT International Preliminary Report on Patentability for PCT/EP2012/074292, mail date Jun. 19, 2014.
Goldman, Maurice et. al., Design and implementation of 13C hyper polarization from ara-hydrogen, for new MRI contrast agents, Comptes Rendus-Chimie, Elsevier, Paria, FR, vol. 9, No. 3-4, Mar. 1, 2006, pp. 357-363, XP024979705.
Goldman, Maurice et al., Hyperpolarization of 13C through order transfer from parahydrogen: A new contrast agent for MRI, Magnetic Resonance Imaging, Elsevier Science, Tarrytown, NY, US, vol. 23, No. 2, Feb. 1, 2005, pp. 153-157, XP004843472.
Golman, K. et. al., Molecular imaging using hyperpolarized 13C, The British Journal of Radiology 2003, vol. 76, Spec No. 2, 2003, pp. S118-S127, XP002538147.
Jamin et al., Magnetic Resonance in Medicine, 2009, 62, pp. 1300-1304.
Joo, Ferenc, Aqueous biphasic hydrogenations, Accounts of Chemical Research Sep. 2002, vol. 35, No. 9, Sep. 2002, pp. 738-745, XP002538144.
Office Action for Japanese App. No. 2013-503125, mail date Oct. 7, 2014 (with English language Office Action Summary) [B0651].
PCT international Search Report and Written Opinion for PCT/EP2011/055485, mail date Jun. 30, 2011.
Reineri, Francesca et. al., New Hyperpolarized contrast agents for 13C MRI from para-hydrogenation of oligooxyethylenic alkynes, Journal of the American Chemical Society 20081112 American Chemical Society US, vol. 130, No. 45, Nov. 12, 2008, pp. 15047-15053, XP002538148.
Wang, Chao et. al., Broader, greener, and more efficient: recent advances in asymmetric transfer hydrogenation, Chemistry, An Asian Journal Oct. 6, 2008, vol. 3, No. 10, Aug. 27, 2008, pp. 1750-1770, XP002538145.

\* cited by examiner

PROCESS FOR THE PREPARATION OF HYPERPOLARIZED DERIVATIVES FOR USE IN MRI ANALYSIS

CROSS-REFERENCE TO RELATED APPLICATIONS

This application is the national stage application of corresponding international application number PCT/EP2012/070187, filed Oct. 11, 2012, which claims priority to and the benefit of European application no. 11184825.5, filed Oct. 12, 2011, all of which are hereby incorporated by reference in their entirety.

The present invention generally relates to the field of Magnetic Resonance Imaging (MRI). More particularly, the invention relates to a process for the preparation of hyperpolarized carboxylic acids ready for use in in-vivo MR diagnostic imaging.

BACKGROUND OF THE INVENTION

MRI is a non invasive technique with broad diagnostic value. The technique has gained wide clinical acceptance and is of great importance in diagnostic medicine. However, despite significant technological advancements (increasing field strength and improvement in technology), applications of MRI are limited by an intrinsically low sensitivity.

Some alternatives to enhance its sensitivity have been developed which involve ex-vivo nuclear spin polarization of agents, prior to administration and consequent in-vivo MR signal measurement.

EP1544634 discloses some of said alternative techniques, comprising among others, Dynamic Nuclear Polarisation (DNP), Para Hydrogen Induced (PHI) polarisation and Polarisation Transfer (PT) from a hyperpolarised noble gas.

U.S. Pat. No. 6,466,814 describes a method of magnetic resonance investigation comprising the production of a hyperpolarised solution of a proper high T1 agent, selected from a series of possible candidates, followed by the administration of said solution to a subject.

During hyperpolarisation of a sample (particularly as regards the DNP methods), very low temperature are often required in order to have the sample polarised in a proper solid form. In this respect, it is known in the art (see e.g. US2008095713) that successful polarization levels are generally achieved by DNP technique when the sample upon freezing forms a so called "glass" form, rather than a crystallized form. It is noticed that it can happen that carboxylic organic acids are not capable of forming a glass in their pure form as such, thus requiring the addition of a glass-forming agent thereto. In this respect, commonly used glass-forming agents, such as inter alia DMSO, may pose some tolerability issues upon in-vivo injection. Even further, the addition of a glass-forming agent generally results in low concentrations with respect to the initial molecule to be hyperpolarised.

We have now found that when a carboxylic organic acid, which is not able to form by itself a glass form upon freezing, is admixed with a suitable precursor thereof, this latter actually acts as a glass-forming agent. In particular, it has been noticed that the addition of a proper precursor to the corresponding starting carboxylic acid leads to the formation of a mixture which is able to form, upon freezing, a proper glass form, suitable for DNP experiments.

Hence, according to the invention, the use of e.g. an anhydride or an ester as glass-forming agent for the corresponding acid derivative is particularly advantageous. We have further observed that said glassed mixture when contacted with an aqueous carrier can be readily transformed in to a final solution mainly containing the starting carboxylic acid in a polarised form.

For these and other advantages which may be better appreciated by the skilled person upon reading the detailed description of the invention, the present invention provides a substantial innovative contribution over the state of the art.

SUMMARY OF THE INVENTION

A first aspect of the invention relates to a process for preparing a hyperpolarized carboxylic organic acid for use in a method of magnetic resonance investigation, which comprises the steps of:

a) preparing a mixture of said carboxylic organic acid with a precursor thereof that upon contact with an aqueous carrier provides at least said acid;

b) subjecting the mixture of step a) to dynamic nuclear polarisation (DNP) methods, to obtain an hyperpolarized mixture; and c) contacting the hyperpolarized mixture of step b) with an aqueous carrier to transform the precursor in the hyperpolarized carboxylic organic acid.

Preferably, the acid is in a neutral form.

Preferably the precursor is an anhydride or an ester of the starting organic acid of choice.

In another aspect, the invention refers to the use of a precursor, preferably a organic anhydride or ester, as glass-forming agent for the corresponding organic acid in dynamic nuclear polarisation (DNP) experiments.

Typically, the carriers are selected from aqueous carrier such as: ionised water and saline solution, optionally comprising one or more additives, such as acids and bases, a buffer, an enzyme and the like.

In another preferred embodiment, the transformation of the mixture into the active organic acid according to the step c) is effected by hydrolysis, optionally in the presence of an enzyme. Examples of suitable enzymes are esterases (generally indicated with EC 3.1.x.x), being carboxylic esterases (EC 3.1.1.1) particularly preferred. In another aspect, the present invention relates to a method for operating an MRI system comprising the steps of:

a) submitting a subject, which has been positioned in said MRI system and treated with a hyperpolarized active acid obtained from a mixture with a corresponding precursor according to the above process, to a radiation frequency selected to excite nuclear spin transitions in a non-zero nuclear spin nuclei of said active substrate; and b) recording a MR signal from said excited nuclei.

In a further aspect, the present invention relates to a method for operating a MRI system comprising the steps of:

a) submitting a subject pre-treated with a hyperpolarized active acid obtained from a mixture with a corresponding precursor according to the above process, which has been positioned in said MRI system, to a radiation frequency selected to excite nuclear spin transitions in a non-zero nuclear spin nuclei of said active substrate; and b) recording a MR signal from said excited nuclei.

DETAILED DESCRIPTION OF THE INVENTION

Figure 1:
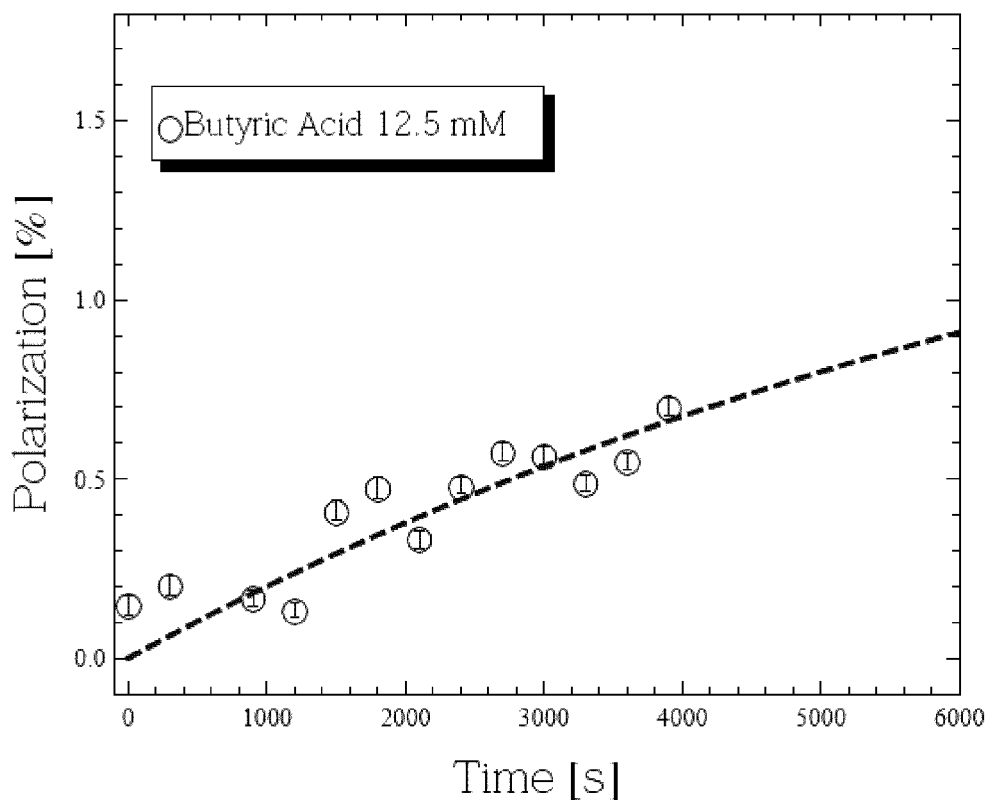
FIG. 1: hyperpolarization curve of a solution (12.5 mM) of butyric acid and finland radical, when hyperpolarized in the absence of any glass-forming agent.
Figure 2:
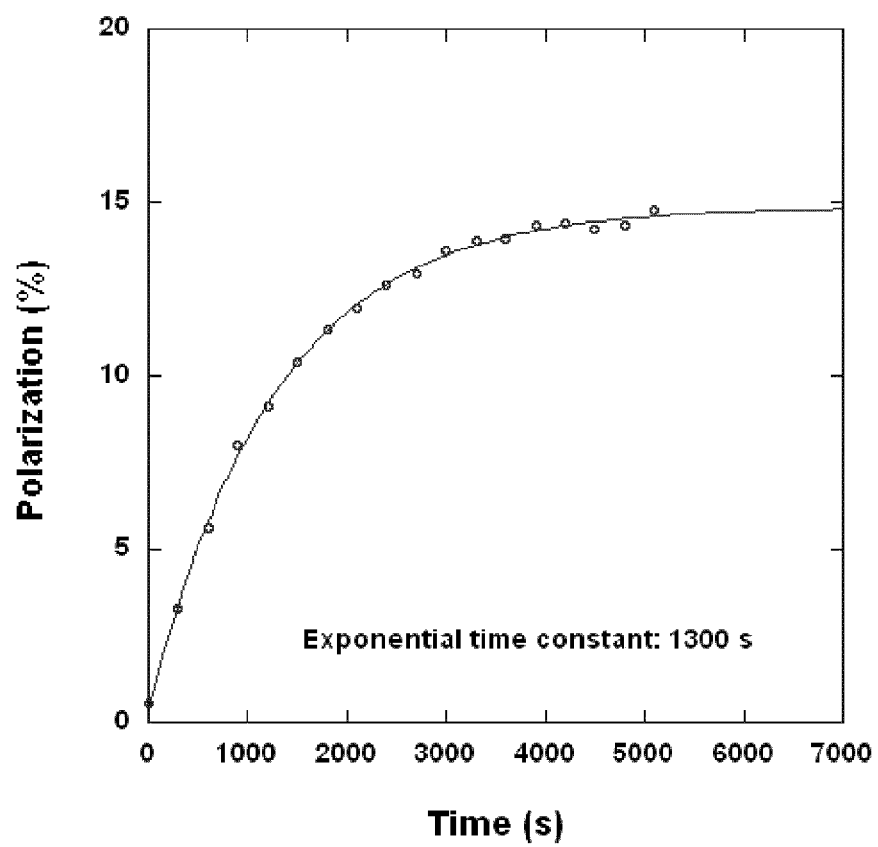
FIG. 2: solid state polarization build-up of a 1:1 mixture (12.5 mM) of 1-13C-propionic acid, propionic anhydride and finland radical.
Figure 3:
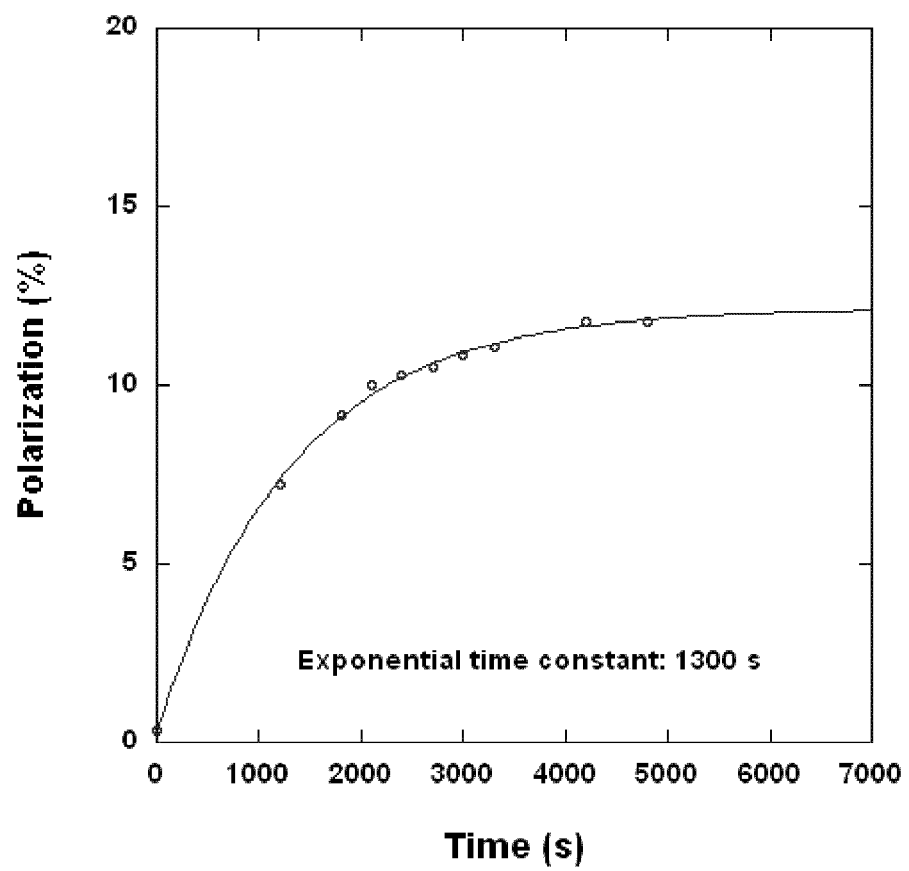
FIG. 3. solid state polarization build up of a 1:5 mixture (12.5 mM) of 1-13C-butyric acid, 1,1-13C-butyric anhydride and finland radical.

The present invention provides an alternative method for the ex-vivo hyperpolarization of carboxylic organic acids, particularly those carboxylic organic acids that need a glass-forming agent to be hyperpolarised. It is in fact known in the art that hyperpolarization (HP) experiments require the substrate to be able to form a so called "glass form" upon freezing. If the substrate on the contrary does not form a proper glass form, an additional glass-forming agent is thus required, in order to obtain the starting substrate as a glass (which will be of course in mixture with said additional glass-forming agent) ready for HP experiments. Surprisingly, we have now found that when the organic acid of choice is admixed with a suitable precursor, the thus formed organic acid/precursor mixture is obtained as a glass form upon freezing without the addition of any further glass-forming agent, as otherwise required. In other words, we have now found that those precursors that upon contact with an aqueous carrier mainly lead to the formation of the starting acid, can be used as glass-forming agents for the corresponding acid substrates in HP experiments, in an efficient and reliable way. The carboxylic acid is preferably chosen among those organic acid substrates that may be used as contrast agent in in-vivo MR analysis, and that are not able to form a glass by themselves when frozen. Generally and according to the invention, the acids are selected from those carboxylic organic acid that are physiologically acceptable and metabolically active in human metabolic pathways, preferably used in their neutral form.

Therefore, the invention refers to a process for preparing a hyperpolarized active organic acid for use in a method of magnetic resonance investigation, which comprises the steps of:

a) preparing a mixture of the carboxylic organic acid of choice with a suitable precursor thereof;

b) subjecting said mixture to dynamic nuclear polarisation (DNP) methods to obtain a hyperpolarized mixture; and c) contacting the thus obtained hyperpolarized (HP) mixture with an aqueous carrier, to transform the HP mixture in the desired hyperpolarized carboxylic organic acid.

The expression "hyperpolarized active substrate" (also referred to as "active carboxylic organic acid" or "active acid" in the following of this specification) comprises within its meaning high T1 organic acid compounds containing non-zero nuclear spin nuclei, capable of exhibiting a long T1 relaxation time. Long T1 relaxation times are to be intended as time values sufficiently long to allow an effective detection of the signal.

The expression "hyperpolarized mixture" comprises within its meaning any hyperpolarized systems containing a given percent of a chosen carboxylic acid and a given percent of a suitable precursor of said carboxylic acid.

Suitable precursors are those compounds that upon contact with an aqueous carrier are converted at least in the starting carboxylic organic acid, typically through a hydrolysis transformation.

The term "glass form" comprises within its meaning a solid solution or an amorphous (non-crystalline) solid form.

The term "glass-forming agent" or "glassing agent" comprises within its meaning a compound which prevents crystallization and promotes the formation of a glass form.

The expression "aqueous carrier" comprises within its meaning any aqueous solvent, solvent mixture or solution that is tolerated by the human or non-human animal body, for use in in-vivo diagnostic applications.

Generally, the carrier is sterile and physiologically tolerable, such as sterile water, purified water such as water for injection (WFI), physiological saline solution, optionally properly buffered. The carrier may optionally comprise a suitable amount of a selected additive (e.g. a base or an acid), capable of promoting the rapid and selective conversion of the hyperpolarized mixture into a water soluble active acid substrate.

In this respect, the additives, when present, are physiologically acceptable ones, and are employed in relatively low amounts, e.g. comprised from 0.1 mole equivalents to 10 mole equivalents, preferably from 1 mole equivalent to 4 mole equivalent (where "mole equivalents" means amount of additive relative to the amount of hyperpolarized precursor), in order to provide physiologically acceptable solutions ready for injection. In some cases, e.g. when the amount of additive added to promote the transformation of the mixture is relatively high, the obtained aqueous solution (comprising the thus obtained hyperpolarized active acid substrate) may subsequently be admixed with further additives in order to render it physiologically acceptable for in-vivo diagnostic applications. For instance, the pH of the solution may subsequently be adjusted at physiologically acceptable values by adding suitable acid or basic buffers. In this respect, examples of suitable additives are pH regulating agents such as organic or inorganic bases (e.g. alkaline metal bases) or organic or inorganic acids or buffers.

As used herein the term "hydrolysis" comprises a chemical reaction in which water reacts with a starting compound to produce one or more resulting compound(s); it typically involves the splitting of a bond, in particular a covalent bond, e.g. on the starting anhydride or ester, and the addition of a hydrogen and/or hydroxide to the structure of the starting compound, to obtain the resulting acid(s).

Said hydrolysis reaction can be carried out under acidic (pH<7), basic (pH>7) or even neutral conditions (pH=7), whereas basic conditions are preferred, as will be described herein below in more details. In this direction, and as previously mentioned, the selected aqueous carrier can contain as additive either a suitable amount of alkaline base such as hydroxides or carbonate, like NaOH or $NaHCO_3$, or $Na_2CO_3$, as well as other organic or inorganic compounds such as trimethylol aminomethane, also known as tromethamine, or trisodium phosphate; or an inorganic or organic acid capable of promoting the hydrolysis of a hyperpolarized precursor such as, among others, phosphoric acid, hydrochloric acid, citric acid or acetic acid.

Particularly preferred additives for the method of the instant invention are sodium hydroxide (NaOH) or hydrochloric acid (HCl).

According to a particular preferred embodiment, an aqueous solution of a hyperpolarized mixture (e.g. an anhydride/acid or an ester/acid mixture) in a 10-100 mM concentration is hydrolyzed in the presence of 10-400 mM NaOH. The hydrolysis of the hyperpolarised mixture practically occurs by adding the same to a carrier selected as formerly described, at a temperature from about 20° C. to 100° C., preferably from 40° C. to 70° C., to obtain an aqueous solution mainly containing the thus obtained hyperpolarised active acid. To this extent, the HP mixture shall be capable of being quantitatively transformed into the desired hyperpolarized active substrate upon contact with the aqueous carrier, as formerly described.

In the present application, the expression "quantitative transformation" is intended to indicate a transformation (preferably a hydrolysis) in the amount of 20% or more, preferably 50% or more, more preferably 75% or more, and even more preferably of at least 90%, being a transformation of at least 95% of the precursor into the active acid particularly preferred.

As afore mentioned, the process of the invention is particularly advantageous for the preparation of those hyperpolarized carboxylic organic acids that do not form a glass by themselves upon freezing, thus needing the use of at least an additional glass-forming agent. It has to be noted, that when such glass-forming agent is employed, it may have to be removed from the final solution before injection of the thus obtained hyperpolarised solution.

Unexpectedly, the mixtures of said carboxylic organic acid with a suitable precursors thereof according to the present invention, are indeed able of forming said required glass form, without the need of any further glass-forming agent. It has to be noted that the use of said precursors, particularly the anhydride or ester, as glass-forming agent is advantageously not only because the employment of any additional glass-forming agent (e.g. DMSO) is avoided, but also because high concentrations of the desired hyperpolarised acid can be achieved upon contact of the hyperpolarised mixture with an aqueous carrier, as defined in step c).

In more detail, according to all the above preferred embodiments, preferred mixtures comprise a selected organic acid and one or more corresponding precursor that is transformed in said selected organic acid upon contact with an aqueous carrier.

Examples of Suitable Precursors are:

1a)

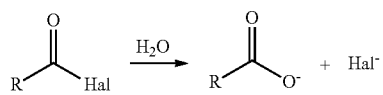

wherein Hal is an halogen atom (F, Cl, Br, I), and R is a C1-C10 alkyl or alkene, cycloalkyl or cycloalkene, arylalkyl or heteroarylalkyl radical, optionally branched and/or substituted:

1b)

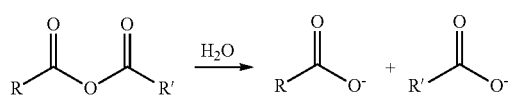

wherein R is as defined in point 1a) above, and R' is an alkyl, aryl, cycloalkyl, aryl radical (or any of its combination) which by hydrolysis leads to the release of RCOOH and R'COOH, R'COOH being either the same as RCOOH (symmetric anhydrides) or is a different physiologically acceptable carboxylic acid (mixed anhydrides); in this latter case, it can be a different active substrate, a pharmaceutically active compound or simply a non-toxic substance (where "non-toxic substance" as herein defined identifies compounds with an LD50>0.1 mmol/Kg);

1c)

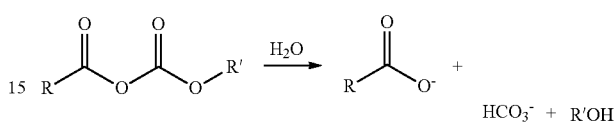

wherein R is as defined in point 1a) above, and R' is an alkyl, aryl, cycloalkyl, aryl radical (or any of its combination) which by hydrolysis lead to the release of RCOOH and R'OH, where R'OH is an hydroxyl- or emiacetal-functionalized physiologically acceptable compound (i.e. different active substrate, a pharmaceutically active compound or a non-toxic substance);

1d) Compounds of General Formula:

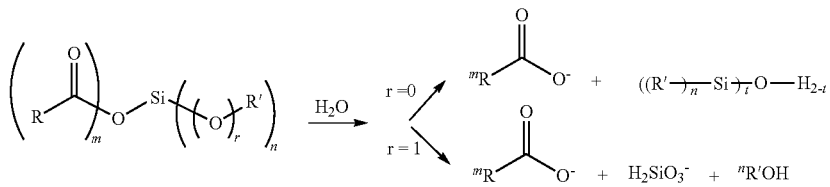

wherein R is as defined in point 1a) above, and R' is defined as in point 1b) or hydrogen; m+n=4; r=0-1; t=1-2 and the silicon-containing molecule is a physiologically acceptable compound or is easily and rapidly removed by methods known in the art;

1e)

wherein R is as defined in point 1a) above;

2) Esters and Hydrolyzed Substrates of the General Formula:

wherein R is defined as in point 1a) above, and R' as defined in point 1b) above;

3) Lactones of General Formula:

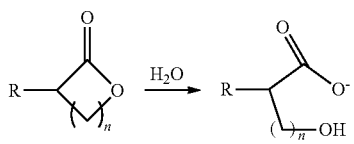

where R is defined as in point 1a) above, and n=0-3.

Particularly preferred examples of said precursors include, but are not limited to anhydrides either symmetric or mixed, such as butyric anhydride and butyric-acetic anhydride and ester derivatives e.g. ethylsuccinate (mono or di-ester), 2-oxoglutarate ethyl ester (mono or di-ester), ethylmalate (mono or di-ester).

Examples of suitable organic acids include those listed above, obtainable by the previously illustrated precursors. In more detail, preferred organic acids include, carboxylic acids, including mono-, di- and tri-carboxylic acids both in their dissociated (preferably) or undissociated form, optionally containing one or more of the following moieties: hydroxyl (hydroxy acids), carboxy (ketoacids). Examples of suitable carboxylic acids (preferably in their carboxylic acid form) include:

R—COOH, where R represents $C_1$-$C_{10}$ alkyl, $C_1$-$C_{10}$ oxo-alkyl, $C_1$-$C_{10}$ hydroxy-alkyl, $C_1$-$C_{10}$ amino-alkyl, $C_1$-$C_{10}$ alkene, R—(COOH)$_2$, where R represents $C_1$-$C_{10}$ alkyl, $C_1$-$C_{10}$ oxo-alkyl, $C_1$-$C_{10}$ hydroxy-alkyl, $C_1$-$C_{10}$ amino-alkyl, $C_1$-$C_{10}$ alkene, and where the carboxylic groups are bound to two different carbon atoms of R;

R—(COOH)$_3$, where R represents $C_1$-$C_{10}$ alkyl, $C_1$-$C_{10}$ oxo-alkyl, $C_1$-$C_{10}$ hydroxy-alkyl, $C_1$-$C_{10}$ amino-alkyl, $C_1$-$C_{10}$ alkene, and where the carboxylic groups are bound to three different carbon atoms of R;

Specific examples of high T1 hyperpolarized organic acids include, for instance, butyric acid, 2-oxobutyric acid, 2-hydroxybutyric acid, (R)-3-hydroxybutyric acid, crotonic acid, succinic acid, oxaloacetic acid, malic acid, fumaric acid, citric acid, isocitric acid. Examples of suitable organic acids are disclosed for instance in U.S. Pat. No. 6,278,893, here incorporated by reference.

Preferred hyperpolarized organic acid/precursor systems are selected from: butyric acid/butyric anhydride, succinic acid/succinate mono ethyl ester, 2-oxoglutaric acid/2-oxoglutarate mono ethyl ester, malic acid/malate mono ethyl ester, pyroglutamic acid/pyroglutamate ethyl ester, 2-oxothiazolidine-4-carboxylic acid/2-oxothiazolidine-4-carboxylate ethyl ester.

In one preferred embodiment, the mixture contain the organic acid of choice and one corresponding symmetric or mixed anhydride.

"Symmetric anhydrides" means those anhydrides of formula (I):

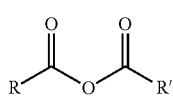

wherein R and R' are the same; whereas "mixed anhydrides" means those anhydrides of the above formula (I) wherein R and R' are different. Examples of symmetric anhydrides are: acetic anhydride (i.e. R=R'=CH$_3$—), propionic anhydride (i.e. R=R'=CH$_3$CH$_2$—) and the like. Examples of mixed anhydrides are propyl acetic anhydride (i.e. R=CH$_3$— and R'=CH$_3$CH$_2$—) and the like.

Preferred symmetric anhydride/acid mixtures are mixtures comprising a carboxylic acid of formula (A):

R—COOH    (A);

and at least a symmetric anhydride of formula (I):

wherein R and R' are the same, selected from: C1-C20 linear or branched alkyl group, satured or unsaturated, optionally substituted, preferably a C1-C10 linear or branched alkyl group optionally substituted, even more preferably a linear or branched C1-C6 alkyl group optionally substituted.

The term C1-C20, C1-C10, C1-C6 linear or branched alkyl means an aliphatic alkyl chain containing respectively from 1 to 20, from 1 to 10 or from 1 to 6 Carbon atoms, either linear or branched. Examples of C1-C6 alkyl groups are: methyl, ethyl, propyl, butyl and the like.

More preferred acid/anhydride mixtures are: acetic acid/acetic anhydride, propionic acid/propionic anhydride, or butyric acid/butyric anhydride, octanoic acid/octanoic anhydride or palmitic acid/palmitic anhydride.

In a another preferred embodiment, the mixture comprises a carboxylic acid of formula (A):

R—COOH    (A);

and at least a mixed anhydride of formula (I):

wherein R and R' are differently and independently selected from: C1-C20 linear or branched alkyl group, satured or unsaturated, optionally substituted, preferably a C1-C10 linear or branched alkyl group optionally substituted, even more preferably a linear or branched C1-C6 alkyl group optionally substituted.

The term C1-C20, C1-C10, C1-C6 linear or branched alkyl means an aliphatic alkyl chain containing respectively from 1 to 20, from 1 to 10 or from 1 to 6 Carbon atoms, either linear or branched. Examples of C1-C6 alkyl group are: methyl, ethyl, propyl, butyl and the like.

Examples of preferred acid/mixed anhydride mixtures are: acetic acid or propionic acid in mixture with propionic-acetic anhydride.

In a further embodiment of the invention, the mixture comprises a carboxylic acid of formula (A):

R"—COOH    (A);

and
at least a mixed anhydride of formula (I):

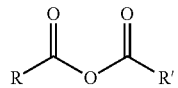
(I)

wherein R" is different from R and R', and R, R' and R" are independently selected from: a C1-C10 linear or branched alkyl group optionally substituted, even more preferably a linear or branched C1-C6 alkyl group optionally substituted. Examples of C1-C6 alkyl group are: methyl, ethyl, propyl, butyl and the like.

According to a preferred embodiment, the transformation of the hyperpolarized precursor in the mixture into the active acid according to step c) is effected by hydrolysis, and even more preferably, the enzymatic hydrolyzed precursor is an hyperpolarized ester.

In a preferred embodiment of the invention, the organic acid of choice is the butyric acid and the mixture is butyric acid/butyric anhydride mixture. Butyric acid is a metabolite in the fatty acid metabolic pathways.

Butyric acid however crystallizes upon rapid freezing as indicated in herewith included experimental part. Hence, it is necessary to add a certain amount of a glass-forming agent (e.g. glycerol or DMSO) in order to obtain the butyric acid in a proper glass form suitable for the DNP experiment. The fact of admixing butyric acid with DMSO practically reduces the final concentration of the acid in the DNP-preparation. On the contrary, butyric acid forms a glass upon rapid freezing, and suitable for DNP transformation, when mixed with the corresponding anhydride, e.g the butyric anhydride, according to the present invention.

Upon dissolution in an aqueous solution at basic pH (e.g. an aqueous solution with one molar equivalent of a base such as NaOH) the hydrolysis of the thus formed acid/anhydride mixture proceeds rapidly, leading to a final solution substantially containing only the hyperpolarized butyric acid. Of note, in fact, the hydrolysis of the butyric anhydride as glassing agent in the hyperpolarized mixture, provides twice the amount of butyric acid molecules, thus allowing to obtain an at least a double concentration of butyric acid.

Similarly, also mixture of the butyric acid with mixed butyric-acetic anhydride forms a glass upon rapid freezing without the use of any additional glass-forming agents. Also in this case, the hydrolysis of the hyperpolarized mixture proceeds rapidly upon contacting said mixture with an aqueous solution containing e.g. one molar equivalent of NaOH. In this latter case, it can be appreciated that the hydrolysis of the mixed anhydride provides a similar amount of an additional hyperpolarized substrate (i.e. acetic acid), in addition to the butyric acid.

In a still further preferred embodiment, the invention refers to a process for preparing a hyperpolarized carboxylic organic acid for use in a method of magnetic resonance investigation, which comprises the steps of:

a) preparing an mixture of said carboxylic organic acid with an ester;

b) subjecting said mixture to dynamic nuclear polarisation (DNP) methods to obtain an hyperpolarized mixture; and c) contacting the obtained hyperpolarized mixture with an aqueous carrier to transform it into the hyperpolarized active carboxylic organic acid.

In more detail, the mixture comprises the selected carboxylic organic acid of formula (A):

and
at least an ester derivative of formula (II)

wherein R is as above defined, and R' is a C1-C6 linear or branched alkylic group such as, e.g.: methyl, ethyl, propyl, butyl and the like. Preferably the ester derivative is selected among those esters of formula (II) that upon hydrolysis lead to the desired carboxylic acid and pharmaceutically acceptable side products.

Preferably the R' group in the above formula (II) is ethyl, i.e. —C2H5.

In this direction, preferred acid/ester mixture are selected from: malic acid/maleate monoethyl ester, malic acid/maleate diethylester, acetic acid+ethyl acetate. Preferably, the precursor/acid mixture comprises the acid of choice in admixture with one precursor thereof, preferably with one anhydride or with one ester derivative. In a preferred embodiment, the acid and the precursor thereof are present in a molar ratio of 1:10 to 10:1. Preferably, the carboxylic organic acid according to the invention, is present in the precursor mixture, such as the acid/anhydride or acid/ester mixture, in an equimolar 1:1 ratio (which means 1 mole of acid and one mole of anhydride or ester) or even more preferably, in an molar defect with respect to the corresponding anhydride or ester. Accordingly, preferred mixtures contain the acid in a molar ratio with respect to the anhydride or ester ranging from 1:2 to 1:7, more preferably from 1:3 to 1:5. For instance, when the acid and the precursor are liquids and the mixture is a 1:3 (v/v) mixture of propionic acid and propionic anhydride, or a 1:1 (v/v) mixture of propionic acid and propionic anhydride, or a 1:7 (v/v) mixture of butyric acid and butyric anhydride, or a 1:5 mixture of butyric acid and butyric anhydride.

As afore mentioned, for each preferred embodiment of the present invention, the hyperpolarised mixture of step b) provides, generally upon hydrolysis reaction according to step c), a corresponding carboxylic acid, alone or in admixture with one or more side reaction product, the latter preferably being pharmaceutical acceptable.

Preferably, at least one mixture component (e.g. the anhydride, the ester or the starting acid) is enriched with non-zero nuclear spin nuclei, such as 13C, 19F and/or 15N nuclei, even more preferably, both the acid and the precursor such as anhydride or ester are enriched, even more preferably, enriched with 13C.

The term "enriched" means that the concentration of the non-zero spin nuclei in the compound is above the typical value of natural abundance of said nuclei, preferably above at least 10% of natural abundance, more preferably above at least 25%, and even more preferably above at least 75% of its natural abundance and most preferably above at least 90% of its natural abundance. The enrichment will in particular be concentrated on an atom position, for which a chemical transformation of the molecule, or a chemical or magnetic changes of the environment of the molecule, will be measurable as a change of its chemical shift. Said non-zero nuclei confer to the substrate a T1 relaxation time of at least 5 seconds (indicated with s), preferably of at least 10 s, preferably of at least 20 s, preferably of at least 30 s, and even more preferably of at least 40 s, measured in a solution subjected to a magnetic fields of from about 0.5 mT to about 20 T (Tesla). The enrichment may include either selective enrichments of one or more sites within the molecule or uniform enrichment of all sites. To this extent, commercially available enriched precursors, such as commercially available enriched anhydrides or esters, can be suitably employed or, in case, the enrichment of choice can be achieved by chemical synthesis, or biological labeling, according to well known prior art teachings.

Being obtained from the mixture e.g. with the respective anhydride and/or ester, the active substrates will correspondingly be enriched with respective non-zero nuclear spin nuclei, such as 13C, 19F and/or 15N nuclei, preferably 13C.

It has to be noted that the signal of any hyperpolarized imaging agent decays due to spin relaxation. Hence, the final hyperpolarized active acid, particularly when in solution, shall maintain its polarization for a sufficiently long period of time, in order to allow the imaging procedure to be carried out within a relatively comfortable frame of time. Preferably, the T1 value of the hyperpolarized precursor and of the hydrolyzed acid shall thus be of at least 5 seconds or higher, preferably of 10 s seconds or higher, more preferably at least 30 s seconds and even more preferably of 50 s seconds or higher. Particularly preferred are those substrates for which the T1 value is of 70 s seconds or higher, and even more particularly preferred are those having a T1 value of 100 seconds or higher. Said T1 values are referred to values measured typically at a field strength of from 0.5 mT to 20 T and at a temperature of from 25° C. to 70° C., in particular at a field strength of 1.5-3 T and at a temperature of 37° C. When outside the body, said T1 values are generally measured at a field strength of 0.5 mT and at a temperature of 60° C. According to a further embodiment, the above mentioned non-zero spin nuclei can be directly linked to one or more Deuterium atom, typically with the intention to prolong the T1 values of the final hyperpolarized compound (see in this direction, US 2008/0287774 A1, herein included by reference). By that, many more metabolites can advantageously be distinguished from their substrates on the basis of the larger chemical shift dispersion thus available, and, even more advantageously, the Deuteration of hyperpolarized non-zero nuclear spins can expand the group of possible non-zero nuclear spins useful for the imaging of final hyperpolarized compounds and their metabolites. Remarkably, the active acids obtained from the corresponding hyperpolarized mixture, according to the present invention, are in particular capable of exhibiting a change in chemical shift in response of a change of physiological conditions (e.g. changes in the pH, $pO_2$, $pCO_2$, redox potential, temperature or ionic concentrations in the vascular system) or a consequence of metabolic activities, such as cellular uptake, cytosolic reactions such as transaminase reactions (comprising amino acids e.g. aspartate and keto acids e.g. oxaloacetate) and glycolysis (comprising carbohydrates e.g. glucose), mitochondrial reactions such as TCA cycle reactions (comprising molecules which are hydrated e.g cis-acontate), redox reactions (comprising ketobodies e.g. acetoacetate) or betaoxidations (comprising short and medium chain fatty acids e.g. butyrate).

Preferred active substrates will for instance exhibit a chemical shift difference of more than 1.5 ppm for quaternary carbon, 2.1 ppm for deuterate methine, 4.2 ppm for deuterated methylene, and 5.4 ppm for deuterated methyl groups, at a filed of 3 T.

According to the invention, the hyperpolarized mixture of step b) is obtained by Dynamic Nuclear Polarisation (DNP) methods, in the presence of a polarizing agent, as described, for instance, in WO-A-99/35508. Due in particular to their efficient polarization properties, the use of trityl radicals as polarizing agents is preferred, such as, for instance those described in WO-A-99/35508, WO-A-88/10419, WO-A-90/00904, WO-A-91/12024, WO-A-93/02711 or WO-A-96/39367 and herein included by reference.

Briefly, the process comprises in general terms the steps of:

(a) preparing a mixture of the selected acid with a suitable precursor such as an anhydride or an ester thereof;

(b) mixing the mixture of point (a) with a polarizing agent (c) exposing the mixture of point (b) to a microwave irradiation of a frequency, properly selected to excite electron spin transitions in said polarizing agent;

(d) dissolving said DNP preparation in an aqueous carrier (hyperpolarized solution) to obtain the desired hyperpolarised organic acid; and optionally (e) removing the polarizing agent from the hyperpolarized solution.

An efficient DNP process (c) is best obtained at high magnetic field (3-8 T) and low temperatures (0.5-4° K), typically obtaining a level of polarization of at least 1%, preferably of at least 5% and even more preferably of at least 10%, where polarization is defined by the following equation:

$$P = \frac{N\alpha - N\beta}{N\alpha + N\beta}$$

wherein;

Nα is the number of spins in nuclear spin state α; and

Nβ is the number of spins in nuclear spin state β.

The polarizing agent needs to be stable and soluble in the preparation of the high T1 precursor and in an optional admixed glass former in order to obtain a homogenous distribution and an optimal concentration of the electron spin relative to the nuclear spin. Typically, the polarizing agent is added in an amount of from 5 mM to 50 mM to the mixture undergoing DNP, more preferably from 8 to 18 mM.

According to a still preferred embodiment, a radical of the following general formula (I) can advantageously be employed as polarizing agent:

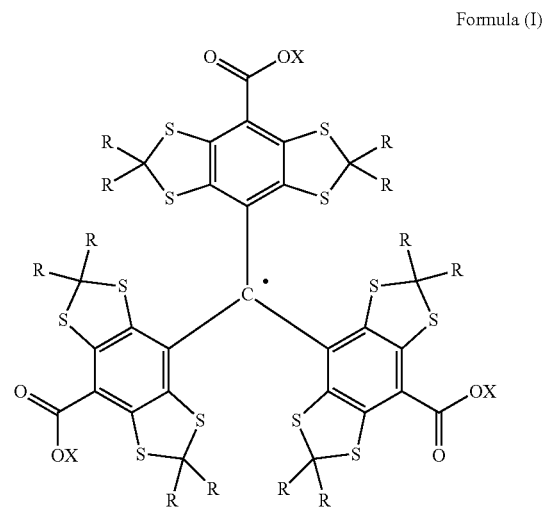

Formula (I)

wherein:

R the same or different, represents a straight chain or branched C1-C6-alkyl group optionally substituted by one or more hydroxyl group, methoxy group, or a group of formula —(CH$_2$)$_n$—O—R2, wherein n is 1, 2 or 3;

R2 is a straight chain or branched C1-C6-alkyl group, optionally substituted by one or more hydroxyl groups or methoxy groups; and X is independently selected from: H; an alkaline metal, e.g. Na, K, Cs; an optionally substituted straight or branched C1-C6 alkyl group, optionally interrupted by Sulphur or Oxygen atoms; or an optionally substituted aliphatic or aromatic C3-C8 cyclic group or hetero group.

Preferably, said radical is a compound of the above formula (I) which is soluble in organic liquid precursors to make at least 5 mM solutions e.g. a compound of formula (I), wherein X is hydrogen, or wherein X is selected from hydrophobic moieties such as methyl, ethyl, ter-butyl or phenyl. Also preferred are radicals of the above formula (I) wherein X is an alkaline metal. Also preferred are said radicals, which are insoluble in water, e.g. a compound of formula (I), wherein both X and R are hydrophobic moieties.

The addition of paramagnetic metal ions is known in the art to increase polarisation levels in the compound to be polarised. (see e.g. WO-2007/064226.

As above mentioned, the hyperpolarized mixture obtained according to step b) of the present process, is contacted with an aqueous carrier, preferably undergoing a hydrolysis reaction. In this direction, and according to another embodiment of the invention, the transformation of the hyperpolarized mixture into the active carboxylic acid substrate according to the step c) of the present process can also be effected in the presence of an enzyme. As used herein the term "enzymatic hydrolysis" comprises an enzymatic reaction in which the speed of the hydrolysis reaction is accelerated and/or the conversion yield of the hydrolysis reaction is increased, for instance with an increase in the conversion yield of at least twice, preferably at least 10 times with respect to the non-enzymatic hydrolysis, resulting in a quantitative (e.g. at least 50%, preferably at least 75% and even more preferably 95%) conversion of the starting mixture to produce one or more resulting compound(s). According to this embodiment of the invention, the hyperpolarized mixture of step b) is contacted with an aqueous carrier as previously defined, at a temperature sufficiently high to melt and dissolve the hyperpolarized sample and to bring it to a temperature of about 40-60° C. Following dissolution, the component of the mixture, e.g. the ester, with the corresponding carboxylic acid is transformed, typically by enzymatic hydrolysis thereof, into the corresponding hyperpolarized carboxylic acid and the obtained solution, optionally after removal of the polarizing agent and/or other by-products of the anhydride or ester's transformation, is administered to the patient, as required. The selected acid mixture can be suitably enzymatically hydrolyzed to at least 50%, preferably at least 75%, even more preferably up to more than 95%.

Preferably, the process of the invention according to step c) refers to the enzymatic hydrolysis of an ester/carboxylic acid mixture.

The amount of the enzyme can vary depending on the specific activity of the particular enzyme, whereas typical amounts are from about 50 U to 60 KU, preferably from 60 U to 600 U, even more preferably from 90 to 270 U/mg enzyme; said amounts added to achieve hydrolysis generally within 2 minutes or even faster, e.g. within 10 seconds.

Also, the enzymes are physiologically acceptable in the relatively low amounts used in the invention. In some cases, e.g. when the amount of additive added to promote the transformation of the precursor is relatively high, the enzyme in the aqueous solution (comprising the hyperpolarized active substrate) may subsequently be removed, e.g. by any method known in the art (such as ion-exchange or size separation), or the applied enzyme may have been immobilized before being used, and it can therefore be filtered off before the administration of the hyperpolarized product. Examples of employable enzymes can be selected among those enzymes that perform the hydrolysis of the hyperpolarized acid mixture within the concentrations (expressed for instance in mM) and on the time-scale of the method (expressed in minutes), and which can be found in the class of enzymes called hydrolases, in particular esterases (generally indicated with EC 3.1.x.x, or even with EC 3.1.1.1).

According to a further preferred embodiment, said enzyme is selected from the group consisting of: esterases, where particularly preferred are carboxylic esterases.

The enzymatic hydrolysis can be properly carried out by analogy to the hydrolysis reaction as previously described in the present invention in the absence of the enzyme, e.g. under acid (pH below 7), basic (pH higher than 7) or neutral conditions (pH 7), within the same preferred aqueous carriers as described above.

Preferably, the enzymatic hydrolysis is carried out in buffered aqueous solution at the optimum pH and temperature for the enzyme.

Therefore, in a particular preferred embodiment, the present invention relates to a process for the preparation of hyperpolarised carboxylic acid, comprising the enzymatic hydrolysis of a DNP hyperpolarised mixture of said acid with the corresponding ethyl ester, to afford the final active acid, wherein said hydrolysis is carried out in the presence of esterase at a temperature from 40 to 60° C. and at a pH from 6 to 9. According to a practical embodiment, the enzymatic hydrolysis of a selected hyperpolarized mixture is carried out as follow:

a hyperpolarized mixture of an organic acid with a suitable ester as above defined was hyperpolarized and dissolved in a proper aqueous medium, following procedures described in the art. The thus obtained solution containing the hyperpolarized mixture was optimized for the enzymatic hydrolysis (buffer type, pH and temperature), as previously described. Then, the solution containing the hyperpolarized mixture was mixed with an enzyme solution or immobilized enzyme containing the desired enzymatic activity and, after completed hydrolysis, the enzyme was optionally removed from the reaction medium.

According to the present invention, hyperpolarized compounds obtained e.g. from respective anhydride or esters mixtures as illustrated above, may be monitored using MR spectroscopy or MRI techniques. The analysis can be performed according to common procedures, such as continuous monitoring or single discrete measurements of a series of discrete measurements carried out at suitable intervals of time.

Therefore, in another aspect, the present invention relates to a method for operating an MRI system comprising the steps of:

a) submitting a subject, which has been positioned in said MRI system and treated with a hyperpolarized active acid obtained from a corresponding mixture with a precursor according to the above process, to a radiation frequency selected to excite nuclear spin transitions in a non-zero nuclear spin nuclei of said active substrate; and b) recording a MR signal from said excited nuclei.

In a further aspect, the present invention relates to a method for operating a MRI system comprising the steps of:

a) submitting a subject pre-treated with a hyperpolarized active acid obtained from a mixture with a precursor according to the above process, which has been positioned in said MRI system, to a radiation frequency selected to excite nuclear spin transitions in a non-zero nuclear spin nuclei of said active substrate; and b) recording a MR signal from said excited nuclei.

When the hyperpolarization of the precursor is effected in the presence of a polarizing agent, said polarizing agent is preferably totally or partially separated from the active substrate before administration thereof.

According to the present method, suitable precursors are selected from those hyperpolarized substances which, upon contact with an aqueous carrier are transformed into at least one active substrate, preferably by hydrolysis, as formerly indicated. To this extent, said precursors are preferably: symmetric anhydrides, mixed anhydrides, or esters. The active substrate is generally present in solution, and the pH of the solution may be adjusted at physiologically acceptable values by adding suitable acid or basic buffers thereto, before administration thereof. The precise concentration will of course depend upon a range of factors such as, inter alia, toxicity and administration route. In general, optimal concentrations will in most cases lie in the range from 10 mM to 150 mM, particularly from 40 to 80 mM. In any case, the dosage of the solution should be kept as low as possible whilst still providing a detectable contrast response. The dosage of the MR imaging substrate employed according to the present method will vary depending on, for instance, the nature of the MR imaging agents used, the tissue or organ of interest and the measuring apparatus. The hyperpolarized hydrolysed substrate can be administered into the vascular system or directly into an organ or muscle tissue, or by subdermal or subcutaneous route, as the case may be. Then, according to the present method, the sample is exposed to a uniform magnetic field (also known as "primary magnetic field") with radiation of a frequency selected to excite nuclear spin transitions in said hyperpolarised active substrate. The hyperpolarization of the mixture and, consequently, of the active substrate thereof, results in an increasing in the population difference between the excited and ground nuclear spin states of those nuclei which are responsible for the magnetic resonance signals. Since MR signal intensity is proportional to this population difference, the final detected MR signals result in larger amplitude signals. The amplitude of the induced MR signals is also dependent upon several other factors, such as the strength of the magnetic field, the temperature of the sample, the isotopic nature and chemical environment of the imaging nuclei and the like.

In this direction, the chosen procedures for detecting MR signals are those commonly known in conventional MR scanning, such as, multinuclei scanner detection, fast single shot imaging sequences, EPI, RARE and the like. Similarly, the MR signals obtained in the method of the present invention may be conveniently converted into 2- or 3-dimensional image data, into functional, flow or perfusion data, as well as into physiological or metabolic data (e.g. pH, pCO2, temperature or ionic concentrations), by means of conventional manipulations. In particular, the metabolic conversion of the HP substrate may allow to study metabolic processes in the patient's body and/or provide information on metabolic state of a (healthy or pathological) tissue. It will be clear that the present method should be carried out within the frame of time in which the hyperpolarised active acid remains significantly polarised, shortly after being subjected to the chemical conversion (e.g. hydrolysis) of the precursor within the mixture thereof. Therefore, the administration of such active acid and the subsequent MR measurement are preferably effected as rapid as feasible. This means that the sample, either human or non-human animal body, should be available close to the area in which the polarisation takes place. It has to be noted in this respect that the physical features of the solution to be administered (such as the temperature, density and the like) have to be physiologically tolerable in order to reduce the risks associated with the selected route of administration.

Due to the versatility of the process, particularly as regards the mixed anhydrides, the method of the present invention may find clinical application in a variety of imaging investigations such as, but not limited to, the vascular/angiographic imaging, interventional applications, perfusion mapping or metabolic/molecular imaging.

According to a further aspect, the present invention relates to the use of a carboxylic acid precursor as glass-forming agent for said carboxylic acid, in dynamic nuclear polarisation (DNP) experiments.

In a preferred embodiment, the invention refers to the use of organic anhydrides, symmetric or mixed, or esters as glass-forming agent for the corresponding carboxylic organic acid, in dynamic nuclear polarisation experiments (DNP).

In particular, the invention refers to the use of: acetic anhydride, propionic anhydride, butyric anhydride for the use as glassing agent for the corresponding acetic, propionic and butyric acid.

In a still preferred embodiment, the invention refers to the use of ethyl ester derivatives as glass-forming agent for the corresponding carboxylic acid, where preferred esters are selected as above indicated.

The following examples are intended to better define the invention, without posing any limitation thereof.

EXAMPLES

Example 1

Glassing Properties of Acid-Anhydride Mixtures

An organic acid and its corresponding symmetric anhydride was mixed (v/v) in ratios ranging from 1:10 to 10:1 in total volumes of 100 µl. The mixture was vortexed for complete mixing. A liquid pellet of 20 µl of these mixtures were dropped into liquid nitrogen. An ocular inspection was made of the frozen pellet which would either reveal a transparent pellet (glass) or a non-transparent pellet (crystal). The results summarized in Table 1 show that it is not possible to make a glass of acetic acid and butyric acid alone whereas when mixing in their respective symmetric anhydrides in ratios up to 30% acid and 70% anhydride (v/v) a glass is made. In the case of propionic acid it was not either possible to make a glass with the organic acid alone but mixed with its corresponding symmetric anhydride up to 60% propionic acid to 40% propionic anhydride made a glass.

TABLE 1 acetic, propionic and butyric acid mixed with
their corresponding symmetric anhydrides

| | Glass(+) or crystal (−) |
|---|---|
| Acetic acid/acetic anhydride | |
| 1:9 | + |
| 2:8 | + |
| 3:7 | + |
| 4:6 | − |
| 5:5 | − |
| 6:4 | − |
| 7:3 | − |
| 8:2 | − |
| 9:1 | − |
| 10:0 | − |
| Propionic acid/propionic anhydride | |
| 1:9 | + |
| 2:8 | + |
| 3:7 | + |
| 4:6 | + |
| 5:5 | + |
| 6:4 | + |
| 7:3 | − |
| 8:2 | − |
| 9:1 | − |
| 10:0 | − |
| Butyric acid/butyric anhydride | |
| 1:9 | + |
| 2:8 | + |
| 3:7 | + |
| 4:6 | − |
| 5:5 | − |
| 6:4 | − |
| 7:3 | − |
| 8:2 | − |
| 9:1 | − |
| 10:0 | − |

Example 2

Polarisation of Butyric Acid without any Additional Glass-Forming Agent

A 12.5 mM of radical solution was prepared by mixing 150 µl of labelled butyric acid with 2.18 mg of Finland radical in its sodium salt form.

Solid state NMR experiments were conducted and the hyperpolarised signal was monitored by acquiring a solid state spectrum generated by a radiofrequency (RF) pulse $\alpha=3°$ every $\Delta t=300$ s.

The results are collected in FIG. 1) showing that the butyric acid preparation does not polarize to acceptable level.

Butyric acid by itself forms a crystal if submerged into liquid nitrogen.

Example 3a

DNP Preparation of a 1:1 Mixture of 1-$^{13}$C-Propionic Acid and Propionic Anhydride 1-$^{13}$C-Propionic acid (38.4 mg, 0.512 mmol) and propionic anhydride (39.6 mg, 0.304 mmol) was added to an Eppendorf tube and mixed with (tris{8-carboxyl-2,2,6,6-tetramethyl-benzo(1,2-d:4,5-dS)bis(1,3)dithiole-4-yl}methyl) acid form (1 mg, 0.96 µmol). This preparation made a glass when rapid frozen in liquid nitrogen. In comparison to a preparation containing the acid alone it is possible to make a preparation of the 1:1 mixture of propionic acid and propionic anhydride, which did not crystallize.

Example 3b

DNP Polarization of a 1:1 Mixture of 1-$^{13}$C-Propionic Acid and Propionic Anhydride The composition from Example 2a (38.5 mg, 0.253 mmol 1-$^{13}$C-propionic acid and 0.15 mmol propionic anhydride) was transferred from the Eppendorf tube to a sample cup and the sample cup was inserted into a DNP polariser. The composition was polarised under DNP conditions at 1.2K in a 3.35 T magnetic field under irradiation with microwave (93.915 GHz). The calculated solid state polarization was 15% and the polarization build-up constant was 1200 s.

Example 3c

DNP Dissolution of a 1:1 Mixture of 1-$^{13}$C-Propionic Acid and Propionic Anhydride The sample of the Example 2b was dissolved in 5 ml 40 mM phosphate buffer pH 7.3+100 mg/l EDTA and transferred to a 14.1 T liquid state magnet. A time series of 16 degree 1D $^{13}$C-NMR spectra were recorded with a total delay between the pulses of 3 s. The liquid state polarization was 11% after 15 s transfer time.

Example 4

DNP Preparation and Polarization of a 1:3 Mixture of 1-$^{13}$C-Propionic Acid and Propionic Anhydride Analogously to the procedure of Examples 3a-b, a 1:3 mixture of 1-$^{13}$C-propionic acid (22 mg, 0.293 mmol) and propionic anhydride (68.2 mg, 0.524 mmol) was prepared and hyperpolarized to give a calculated solid-state polarization of 19% and a polarization build-up constant of 1500 s.

Example 5

DNP Preparation, Polarization and Dissolution of a 1:5 Mixture of 1-$^{13}$C-Butyric Acid and Butyric Anhydride Analogously to the procedure of Examples 3a-c a 1:5 mixture of 1-13C-butyric acid (5.7 mg, 64 µmol) and 1,1'-13C2-butyric anhydride (23.3 mg, 145 µmol) was prepared, hyperpolarized and dissolved in the aqueous carrier. The calculated solid-state polarization was 12% and the anhydrate was fully hydrolyzed during the time of the experiment.

Example 6

DNP Preparation and Polarization of a 1:7 Mixture of 1-$^{13}$C-Butyric Acid and Butyric Anhydride Analogously to the procedure of Examples 3a-b, a 1:7 mixture of 1-13C-butyric acid (3.1 mg, 35 µmol) and 1,1-13C-butyric anhydride (21.1 mg, 0.13 mmol) was prepared and hyperpolarized to give a calculated solid-state polarization of 14% and a polarization build-up constant of 700 s.

Example 5

Glassing Properties of Malic Acid-Ethyl Ester Mixtures

An organic acid and its corresponding mono or di-ethyl ester was mixed (w/w). The mixture was sonicated and vortexed for complete mixing. A liquid pellet of 20 µl of these mixtures were dropped into liquid nitrogen. An ocular inspection was made of the frozen pellet which would either reveal a transparent pellet (glass) or a non-transparent pellet (crystal). The results are summarized in Table 2. Showing that it is possible to make a glass of malic acid mixed with either its mono or its di ethyl ester in ratios up to 75% acid to 25% ethyl ester.

TABLE 2

| Malic acid mixed with its mono or di ethyl ester | |
| --- | --- |
|  | Glass(+) or crystal (−) |
| Malic acid/malic acid mono ethyl ester | |
| 20 mg/23 mg | + |
| 32 mg/23 mg | + |
| Malic acid/malic acid di-ethyl ester | |
| 15 mg/15 mg | + |
| 25 mg/15 mg | + |

The invention claimed is:

1. A process for preparing a hyperpolarized carboxylic organic acid for use in a method of magnetic resonance investigation, which comprises the steps of:
   a) preparing a mixture of said carboxylic organic acid and an anhydride or ester precursor thereof that upon contact with an aqueous carrier provides at least said acid;
   b) subjecting the mixture of step a) to dynamic nuclear polarisation (DNP) methods to obtain a hyperpolarized mixture; and
   c) contacting the hyperpolarized mixture of step b) with an aqueous carrier to transform the precursor into the hyperpolarized carboxylic organic acid.

2. The process of claim 1, wherein the mixture comprises a carboxylic organic acid of formula (A):

R—COOH                                              (A);

and
at least an ester derivative of formula (II)

R—COOR'                                              (II), wherein R is selected from: C1-C20 linear or branched alkyl group, saturated or unsaturated, and R' is a C1-C6 linear or branched alkylic group, optionally substituted.

3. The process according to claim 2 wherein, R' is ethyl.

4. The process of claim 2 wherein: the acid is succinic acid, and the ester is mono or di-ethyl succinate, or the acid is 2-oxoglutaric acid and the ester is 2-oxoglutarate mono or di-ethyl ester, or the acid is malic acid and the ester is mono or di-ethylmalate, or the acid is pyroglutamic acid and the ester is pyroglutamate ethyl ester, or the acid is 2-oxothiazolidine-4-carboxylic acid and the ester is 2-oxothiazolidine-4-carboxylate ethyl ester.

5. The process of claim 1, wherein the mixture comprises a carboxylic acid of formula (A):

R—COOH                                              (A);

and
at least a symmetric anhydride of formula (I):

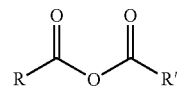

wherein R and R' are the same, selected from: C1-C20 linear or branched alkyl group, saturated or unsaturated, optionally substituted.

6. The process according to claim 5, wherein the acid/anhydride mixture is selected from the group consisting of: acetic acid/acetic anhydride, propionic acid/propionic anhydride and butyric acid/butyric anhydride.

7. The process according to claim 1, wherein the mixture comprises a carboxylic acid of formula (A):

R—COOH                                              (A); and at least a mixed anhydride of formula (I):

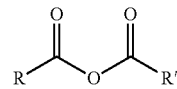

wherein R and R' are differently and independently selected from: C1-C20 linear or branched alkyl group, saturated or unsaturated, optionally substituted.

8. The process according to claim 1, wherein the precursor and the carboxylic organic acid are present in the mixture in a 1:1 molar ratio.

9. The process according to claim 1, wherein said transformation of the precursor according to step c) is effected by hydrolysis of the precursor.

10. The process according to claim 9, wherein the precursor is an ester, and the hydrolysis is performed in the presence of an enzyme.

* * * * *